US007041792B2

United States Patent
Elmore et al.

(10) Patent No.: US 7,041,792 B2
(45) Date of Patent: May 9, 2006

(54) TYPE F BOTULINUM TOXIN AND USE THEREOF

(75) Inventors: Michael J. Elmore, Basingstoke (GB); Margaret L. Mauchline, Shaftesbury (GB); Nigel P. Minton, Salisbury (GB); Vladimir A. Pasechnik, Shrewton (GB); Richard W. Titball, Durrington (GB)

(73) Assignee: Microbiological Research Authority, Wiltshire (GB)

( * ) Notice: Subject to any disclaimer, the term of this patent is extended or adjusted under 35 U.S.C. 154(b) by 331 days.

(21) Appl. No.: 08/981,087

(22) PCT Filed: Jun. 12, 1996

(86) PCT No.: PCT/GB96/01409

§ 371 (c)(1),
(2), (4) Date: May 27, 1998

(87) PCT Pub. No.: WO96/41881

PCT Pub. Date: Dec. 27, 1996

(65) Prior Publication Data

US 2002/0081304 A1 Jun. 27, 2002

(30) Foreign Application Priority Data

Jun. 12, 1995 (GB) .............................................. 9511909

(51) Int. Cl.
*C07K 1/00* (2006.01)

(52) U.S. Cl. ...................... 530/350; 530/300; 435/69.1; 435/320.1; 424/184.1

(58) Field of Classification Search ................. 530/300, 530/350; 435/69.1, 320.1, 252.3; 424/184.1, 424/190.1; 536/23.1; 514/2
See application file for complete search history.

(56) References Cited

U.S. PATENT DOCUMENTS 5,178,859 A * 1/1993 Simon et al. ................ 424/858
5,736,139 A * 4/1998 Kink et al. .............. 424/164.1

FOREIGN PATENT DOCUMENTS

| WO | WO 9403615 | 2/1994 |
| WO | WO 9421684 | 9/1994 |
| WO | WO 94/21684 | * 9/1994 |

OTHER PUBLICATIONS

Lazar et al., Mol.Cell Bio. 8:1247–1252, 1988.*
Burgess et al. J. Cell Bio. 111:2129–2138, 1990.*
East et al, Curr. Microbio. 29:69–77, 08/94.*
Jobling et al Mol Microbiol 517:1765–67, 1991.*
Skolnick et al. Trends in Biotech. 18(1):34–39, 2000.*
Thompson et al. FEMS Microbiol Lttrs. 108 175–82, 1993.*
Wadsworth et al., Biochem J., 268:123–128, 1990.*
Hatheway et al., Applied and Environmental Microbiol., 31(2):234–242, 1976.*
Choh et al., PNAS 77(6):3211–14, 1980.*
Sexton et al., J. of Immunol., 152(4):1861–72. 1994.*
Campbell et al., J. Clin. Microbiol., 31, 2255–2262, 1993 and Genbank Accession No. X70821.*
Elmore et al., Genbank Accession No. L35496, Aug. 23, 1994.*
Montgomery et al., "Evaluation of Botulinum Type F Vaccine By Elisa", Abstracts of the 95th General Meeting of The American Society for Microbiology, 21–25 May 1995, Washington, D.C. USA, p. 289, XP002015937.
Sassenfeld, "Engineering Proteins for Purification", Trends in Biotechnology, vol. 8, No. 4, Apr. 1990, pp. 88–93, XP000103110.
Zhou et al., "Expression and Purification of the Light Chain of Botulinum Neurotoxin A: A Single Mutation Abolishes its Cleavage of Snap–25 and Neurotoxicity After Reconstitution with the Heavy Chain", Biochemistry, vol. 34, Nov. 1995, pp. 15175–15181, XP002015939.

* cited by examiner

*Primary Examiner*—Christine J. Saoud
*Assistant Examiner*—Sharon L. Turner
(74) *Attorney, Agent, or Firm*—Nixon & Vanderhye PC (57) ABSTRACT

A polypeptide free of toxin activity providing protection against *botulinum* type F toxin is provided. A fusion protein of a fragment of a toxin molecule and a purification moiety enabling purification of a fragment from solution and pharmaceutical compositions containing the polypeptide and the fusion protein are described.

28 Claims, 4 Drawing Sheets

FIG. 1

FIRST AMPLIFICATION, FIRST ROUND

FIRST AMPLIFICATION, SECOND ROUND

+FLANKING PRIMERS
[P1 + P2]

SECOND AMPLIFICATION

FIG. 2 pMAL™-c2,-p2:

POLYLINKER malE ... lacZα
rrnB TERMINATOR
P_tac
pMAL-c2
pMAL-p2
AMP^r
lacI^q
M13 ori
pBR322 ori pMAL™-c2,-p2: POLYINKER

Xmnl  EcoRI BamHI Xbal  Sall  Pstl  HindIII
malE..ATC GAG GGA AGG ATT TCA GAA TTC GGA TCC TCT AGA GTC GAC CTG CAG GCA AGC TTG.._lacZα
ile glu gly arg ile
FACTOR Xa CLEAVAGE SITE BoNT/F-H_c EcoRI   Hpal   Mlul   SpII   Xbal 0   0.2   0.4   0.6   0.8   1.0   1.2  1.3-kb

FIG. 3

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 431 amino acids
      (B) TYPE: amino acid
      (C) STRANDEDNESS:
      (D) TOPOLOGY: linear    (ii) MOLECULE TYPE: peptide    (xi) SEQUENCE DESCRIPTION: SEQ ID NO:1:

```
Ser Tyr Thr Asn Asp Lys Ile Leu Ile Leu Tyr Phe Asn Lys Leu Tyr
1               5                   10                  15

Lys Lys Ile Lys Asp Asn Ser Ile Leu Asp Met Arg Tyr Glu Asn Asn
            20                  25                  30

Lys Phe Ile Asp Ile Ser Gly Tyr Gly Ser Asn Ile Ser Ile Asn Gly
            35                  40                  45

Asp Val Tyr Ile Tyr Ser Thr Asn Arg Asn Gln Phe Gly Ile Tyr Ser
        50                  55                  60

Ser Lys Pro Ser Glu Val Asn Ile Ala Gln Asn Asn Asp Ile Ile Tyr
65                  70                  75                  80

Asn Gly Arg Tyr Gln Asn Phe Ser Ile Ser Phe Trp Val Arg Ile Pro
                85                  90                  95

Lys Tyr Phe Asn Lys Val Asn Leu Asn Asn Glu Tyr Thr Ile Ile Asp
                100                 105                 110

Cys Ile Arg Asn Asn Asn Ser Gly Trp Lys Ile Ser Leu Asn Tyr Asn
            115                 120                 125

Lys Ile Ile Trp Thr Leu Gln Asp Thr Ala Gly Asn Asn Gln Lys Leu
            130                 135                 140

Val Phe Asn Tyr Thr Gln Met Ile Ser Ile Ser Asp Tyr Ile Asn Lys
145                 150                 155                 160

Trp Ile Phe Val Thr Ile Thr Asn Asn Arg Leu Gly Asn Ser Arg Ile
                165                 170                 175

Tyr Ile Asn Gly Asn Leu Ile Asp Glu Lys Ser Ile Ser Asn Leu Gly
                180                 185                 190

Asp Ile His Val Ser Asp Asn Ile Leu Phe Lys Ile Val Gly Cys Asn
            195                 200                 205

Asp Thr Arg Tyr Val Gly Ile Arg Tyr Phe Lys Val Phe Asp Thr Glu
            210                 215                 220

Leu Gly Lys Thr Glu Ile Glu Thr Leu Tyr Ser Asp Glu Pro Asp Pro
225                 230                 235                 240

Ser Ile Leu Lys Asp Phe Trp Gly Asn Tyr Leu Leu Tyr Asn Lys Arg
                245                 250                 255

Tyr Tyr Leu Leu Asn Leu Leu Arg Thr Asp Lys Ser Ile Thr Gln Asn
                260                 265                 270

Ser Asn Phe Leu Asn Ile Asn Gln Gln Arg Gly Val Tyr Gln Lys Pro
            275                 280                 285

Asn Ile Phe Ser Asn Thr Arg Leu Tyr Thr Gly Val Glu Val Ile Ile
            290                 295                 300

Arg Lys Asn Gly Ser Thr Asp Ile Ser Asn Thr Asp Asn Phe Val Arg
305                 310                 315                 320
```

-continued

```
Lys Asn Asp Leu Ala Tyr Ile Asn Val Val Asp Arg Asp Val Glu Tyr
                325                 330                 335
Arg Leu Tyr Ala Asp Ile Ser Ile Ala Lys Pro Glu Lys Ile Ile Lys
                340                 345                 350
Leu Ile Arg Thr Ser Asn Ser Asn Asn Ser Leu Gly Gln Ile Ile Val
                355                 360                 365
Met Asp Ser Ile Gly Asn Asn Cys Thr Met Asn Phe Gln Asn Asn
                370                 375                 380
Gly Gly Asn Ile Gly Leu Leu Gly Phe His Ser Asn Asn Leu Val Ala
385                 390                 395                 400
Ser Ser Trp Tyr Tyr Asn Asn Ile Arg Lys Asn Thr Ser Ser Asn Gly
                405                 410                 415
Cys Phe Trp Ser Phe Ile Ser Lys Glu His Gly Trp Gln Glu Asn
                420                 425                 430
```

(2) INFORMATION FOR SEQ ID NO:2:

(i) SEQUENCE CHARACTERISTICS:
        (A) LENGTH: 144 amino acids
        (B) TYPE: amino acid
        (C) STRANDEDNESS:
        (D) TOPOLOGY: linear     (ii) MOLECULE TYPE: peptide     (xi) SEQUENCE DESCRIPTION: SEQ ID NO:2:

```
Ser Tyr Thr Asn Asp Lys Ile Leu Ile Leu Tyr Phe Asn Lys Leu Tyr
1               5                   10                  15
Lys Lys Ile Lys Asp Asn Ser Ile Leu Asp Met Arg Tyr Glu Asn Asn
                20                  25                  30
Lys Phe Ile Asp Ile Ser Gly Tyr Gly Ser Asn Ile Ser Ile Asn Gly
                35                  40                  45
Asp Val Tyr Ile Tyr Ser Thr Asn Arg Asn Gln Phe Gly Ile Tyr Ser
                50                  55                  60
Ser Lys Pro Ser Glu Val Asn Ile Ala Gln Asn Asn Asp Ile Ile Tyr
65                  70                  75                  80
Asn Gly Arg Tyr Gln Asn Phe Ser Ile Ser Phe Trp Val Arg Ile Pro
                85                  90                  95
Lys Tyr Phe Asn Lys Val Asn Leu Asn Asn Glu Tyr Thr Ile Ile Asp
                100                 105                 110
Cys Ile Arg Asn Asn Asn Ser Gly Trp Lys Ile Ser Leu Asn Tyr Asn
                115                 120                 125
Lys Ile Ile Trp Thr Leu Gln Asp Thr Ala Gly Asn Asn Gln Lys Leu
                130                 135                 140
```

(2) INFORMATION FOR SEQ ID NO:3:

(i) SEQUENCE CHARACTERISTICS:
        (A) LENGTH: 144 amino acids
        (B) TYPE: amino acid
        (C) STRANDEDNESS:
        (D) TOPOLOGY: linear     (ii) MOLECULE TYPE: peptide     (xi) SEQUENCE DESCRIPTION: SEQ ID NO:3:

```
Val Phe Asn Tyr Thr Gln Met Ile Ser Ile Ser Asp Tyr Ile Asn Lys
1               5                   10                  15
Trp Ile Phe Val Thr Ile Thr Asn Asn Arg Leu Gly Asn Ser Arg Ile
```

```
                  20                  25                  30
Tyr Ile Asn Gly Asn Leu Ile Asp Glu Lys Ser Ile Ser Asn Leu Gly
            35                  40                  45

Asp Ile His Val Ser Asp Asn Ile Leu Phe Lys Ile Val Gly Cys Asn
 50                  55                  60

Asp Thr Arg Tyr Val Gly Ile Arg Tyr Phe Lys Val Phe Asp Thr Glu
 65                  70                  75                  80

Leu Gly Lys Thr Glu Ile Glu Thr Leu Tyr Ser Asp Glu Pro Asp Pro
                85                  90                  95

Ser Ile Leu Lys Asp Phe Trp Gly Asn Tyr Leu Leu Tyr Asn Lys Arg
               100                 105                 110

Tyr Tyr Leu Leu Asn Leu Leu Arg Thr Asp Lys Ser Ile Thr Gln Asn
            115                 120                 125

Ser Asn Phe Leu Asn Ile Asn Gln Gln Arg Gly Val Tyr Gln Lys Pro
130                 135                 140
```

(2) INFORMATION FOR SEQ ID NO:4:

(i) SEQUENCE CHARACTERISTICS:
        (A) LENGTH: 143 amino acids
        (B) TYPE: amino acid
        (C) STRANDEDNESS:
        (D) TOPOLOGY: linear     (ii) MOLECULE TYPE: peptide     (xi) SEQUENCE DESCRIPTION: SEQ ID NO:4:

```
Asn Ile Phe Ser Asn Thr Arg Leu Tyr Thr Gly Val Glu Val Ile Ile
 1               5                  10                  15

Arg Lys Asn Gly Ser Thr Asp Ile Ser Asn Thr Asp Asn Phe Val Arg
            20                  25                  30

Lys Asn Asp Leu Ala Tyr Ile Asn Val Val Asp Arg Asp Val Glu Tyr
            35                  40                  45

Arg Leu Tyr Ala Asp Ile Ser Ile Ala Lys Pro Glu Lys Ile Ile Lys
 50                  55                  60

Leu Ile Arg Thr Ser Asn Ser Asn Asn Ser Leu Gly Gln Ile Ile Val
 65                  70                  75                  80

Met Asp Ser Ile Gly Asn Asn Cys Thr Met Asn Phe Gln Asn Asn Asn
                85                  90                  95

Gly Gly Asn Ile Gly Leu Leu Gly Phe His Ser Asn Asn Leu Val Ala
               100                 105                 110

Ser Ser Trp Tyr Tyr Asn Asn Ile Arg Lys Asn Thr Ser Ser Asn Gly
            115                 120                 125

Cys Phe Trp Ser Phe Ile Ser Lys Glu His Gly Trp Gln Glu Asn
130                 135                 140
```

(2) INFORMATION FOR SEQ ID NO:5:

(i) SEQUENCE CHARACTERISTICS:
        (A) LENGTH: 1293 base pairs
        (B) TYPE: nucleic acid
        (C) STRANDEDNESS: double
        (D) TOPOLOGY: linear     (ii) MOLECULE TYPE: DNA (genomic)

(xi) SEQUENCE DESCRIPTION: SEQ ID NO:5:

```
TCATATACTA ATGATAAAAT TCTAATTTTA TATTTTAATA AATTATATAA AAAAATTAAA     60

GATAACTCTA TTTTAGATAT GCGATATGAA AATAATAAAT TTATAGATAT CTCTGGATAT    120
```

```
GGTTCAAATA TAAGCATTAA TGGAGATGTA TATATTTATT CAACAAATAG AAATCAATTT      180

GGAATATATA GTAGTAAGCC TAGTGAAGTT AATATAGCTC AAAATAATGA TATTATATAC      240

AATGGTAGAT ATCAAAATTT TAGTATTAGT TTCTGGGTAA GGATTCCTAA ATACTTCAAT      300

AAAGTGAATC TTAATAATGA ATATACTATA ATAGATTGTA TAAGGAATAA TAATTCAGGA      360

TGGAAAATAT CACTTAATTA TAATAAAATA ATTTGGACTT TACAAGATAC TGCTGGAAAT      420

AATCAAAAAC TAGTTTTTAA TTATACACAA ATGATTAGTA TATCTGATTA TATAAATAAA      480

TGGATTTTTG TAACTATTAC TAATAATAGA TTAGGCAATT CTAGAATTTA CATCAATGGA      540

AATTTAATAG ATGAAAAATC AATTTCGAAT TTAGGTGATA TTCATGTTAG TGATAATATA      600

TTATTTAAAA TTGTTGGTTG TAATGATACA AGATATGTTG GTATAAGATA TTTTAAAGTT      660

TTTGATACGG AATTAGGTAA AACAGAAATT GAGACTTTAT ATAGTGATGA GCCAGATCCA      720

AGTATCTTAA AAGACTTTTG GGGAAATTAT TTGTTATATA ATAAAAGATA TTATTTATTG      780

AATTTACTAA GAACAGATAA GTCTATTACT CAGAATTCAA ACTTTCTAAA TATTAATCAA      840

CAAAGAGGTG TTTATCAGAA ACCAAATATT TTTTCCAACA CTAGATTATA TACAGGAGTA      900

GAAGTTATTA TAAGAAAAAA TGGATCTACA GATATATCTA ATACAGATAA TTTTGTTAGA      960

AAAAATGATC TGGCATATAT TAATGTAGTA GATCGTGATG TAGAATATCG GCTATATGCT     1020

GATATATCAA TTGCAAAACC AGAGAAAATA ATAAAATTAA TAAGAACATC TAATTCAAAC     1080

AATAGCTTAG GTCAAATTAT AGTTATGGAT TCAATAGGAA ATAATTGCAC AATGAATTTT     1140

CAAAACAATA ATGGGGGCAA TATAGGATTA CTAGGTTTTC ATTCAAATAA TTTGGTTGCT     1200

AGTAGTTGGT ATTATAACAA TATACGAAAA AATACTAGCA GTAATGGATG CTTTTGGAGT     1260

TTTATTTCTA AAGAGCATGG ATGGCAAGAA AAC                                  1293

(2) INFORMATION FOR SEQ ID NO:6:

(i) SEQUENCE CHARACTERISTICS:
        (A) LENGTH: 1313 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

GGATCCATAT GTCTTACACT AACGACAAAA TCCTGATCCT GTACTTCAAC AAACTGTACA       60

AAAAAATCAA AGACAACTCT ATCCTGGACA TGCGTTACGA AACAACAAA TTCATCGACA       120

TCTCTGGCTA TGGTTCTAAC ATCTCTATCA ACGGTGACGT CTACATCTAC TCTACTAACC      180

GCAACCAGTT CGGTATCTAC TCTTCTAAAC CGTCTGAAGT AAACATCGCT CAGAACAACG      240

ACATCATCTA CAACGGTCGT TACCAGAACT TCTCTATCTC TTTCTGGGTT CGTATCCCGA      300

AATACTTCAA CAAAGTTAAC CTGAACAACG AATACACTAT CATCGACTGC ATCCGTAACA      360

ACAACTCTGG TTGGAAAATC TCTCTGAACT ACAACAAAAT CATCTGGACT CTGCAGGACA      420

CTGCTGGTAA CAACCAGAAA CTGGTTTTCA ACTACACTCA GATGATCTCT ATCTCTGACT      480

ACATTAATAA ATGGATCTTC GTTACTATCA CTAACAACCG TCTGGGTAAC TCTCGTATCT      540

ACATCAACGG TAACCTGATC GATGAAAAAT CTATCTCTAA CCTGGGTGAC ATCCACGTTT      600

CTGACAACAT CCTGTTCAAA ATCGTTGGTT GCAACGACAC GCGTTACGTT GGTATCCGTT      660

ACTTCAAAGT TTTCGACACT GAACTGGGTA AAACTGAAAT CGAAACTCTG TACTCTGACG      720

AACCGGACCC GTCTATCCTG AAAGACTTCT GGGGTAACTA CCTGCTGTAC AACAAACGTT      780
```

-continued

```
ACTACCTGCT GAACCTGCTC CGGACTGACA AATCTATCAC TCAGAACTCT AACTTCCTGA        840

ACATCAACCA GCAGCGTGGT GTTTATCAGA AACCTAATAT CTTCTCTAAC ACTCGTCTGT        900

ACACTGGTGT TGAAGTTATC ATCCGTAAAA ACGGTTCTAC TGACATCTCT AACACTGACA        960

ACTTCGTACG TAAAAACGAC CTGGCTTACA TCAACGTTGT TGACCGTGAC GTTGAATACC       1020

GTCTGTACGC TGACATCTCT ATCGCTAAAC CGGAAAAAAT CATCAAACTG ATCCGTACTT       1080

CTAACTCTAA CAACTCTCTG GGTCAGATCA TCGTTATGGA CTCGATCGGT AACAACTGCA       1140

CTATGAACTT CCAGAACAAC AACGGTGGTA ACATCGGTCT GCTGGGTTTC CACTCTAACA       1200

ACCTGGTTGC TTCTTCTTGG TACTACAACA ACATCCGTAA AAACACTTCT TCTAACGGTT       1260

GCTTCTGGTC TTTCATCTCT AAAGAACACG GTTGGCAGGA AAACTAATCT AGA             1313
```

TYPE F BOTULINUM TOXIN AND USE THEREOF

CROSS REFERENCE TO RELATED APPLICATION

This application claims priority to International Application No. PCT/GB96/01409, filed Jun. 12, 1996, which designates the United States of America.

RELATED ART

The present invention relates to type F *botulinum* toxin, to a fragment of type F *botulinum* neurotoxin, to production of the fragment by recombinant means and to a synthetic gene encoding the fragment. In particular, the invention relates to a novel polypeptide fragment capable of eliciting an immunological response that is protective against type F *botulinum* neurotoxin (BoNT/F) in man or animals and to a vaccine containing the fragment.

*Botulinum* neurotoxins (BoNTs) are high molecular weight proteins (approx. 150,000 Da) which exert potent neuroparalytic effects on vertebrates. They are elaborated by anaerobic Gram-positive bacteria belonging to the genus Clostridium. The majority of clostridia which produce BoNT are classified as *Clostridium botulinum*. In recent years, however, isolates which resemble *Clostridium barati* and *Clostridium butyricum* have been shown to produce BoNT. On the basis of antigenicity, BONT has been subdivided into seven distinct types, designated A to G. All seven neurotoxins (BoNT/A to BoNT/G) are synthesised as a single-chain 150,000 Da molecule which subsequently become nicked to the more potent di-chain form, composed of a heavy (H) chain (approx. 100,000 Da) and a light (L) chain (approx. 50,000 Da) linked by at least one disulphide bridge.

The action of BONT involves three distinct phases. In the first phase the toxins become bound to acceptors on the external surface of the targeted neural cells. This is followed by an energy dependent internalisation step in which the toxin, or part of it, enters the cell. Thereafter, the active moiety of the toxin causes nerve cell dysfunction by blocking the intracellular release of the neurotransmitter, acetylcholine, at the nerve periphery, causing flaccid paralysis. The L chain possesses the catalytic activity responsible for cell poisoning and the H chain delivers this moiety to the cell cytoplasm by mediating binding of the toxin to the cell and subsequent internalisation.

The entire amino acid sequences of all 7 BoNTs are now known (Minton, N. P. (1995), Current Topics in Microbiology and Immunology 195: 161–187), revealing them to be surprisingly divergent in their primary amino acid sequences. Thus, sequence identity amongst the different serotypes generally does not exceed 40%, with those areas of homology localised to discrete domains which are interspersed with amino acid tracts exhibiting little overall similarity. Between the different L chains (average size 439), 63 amino acids are absolutely conserved. Throughout the H chains (average size 843) 97 amino acids are identical. The most notable areas of conservation include: the two cysteine residues involved in the disulphide bond formation between the L and H chain; the histidine rich motif within the L chain associated with metalloprotease activity; and a highly conserved PYI/VXALN-motif found adjacent to regions identified as possessing membrane spanning potential. The most notable tract of sequence divergence amongst toxins is localised to the COOH-terminus of their respective H chains (amino acid 1124 onwards of BoNT/A). This would appear to be consistent with the notion that this domain is involved in neurotoxin binding and that different toxins target different acceptors on neural cell surfaces.

The effectiveness of modern food-preserving processes in Western countries has made outbreaks of botulism extremely rare. The frequent use of *C. botulinum* as a test organism in the food industry, and the growing use of the toxin by neurobiochemists, has, however, increased the need for human vaccines. The formulation of these vaccines has changed little since the early 1950s: partially purified preparations of the neurotoxins are toxoided by formaldehyde treatment and absorbed onto precipitated aluminium salts. Using such methodology, polyvalent vaccines (against ABCDE or ABEF) for human immunisation are currently available. Such vaccines suffer from the drawback of low immune response and considerable batch to batch variation due to the high proportion (60–90%) of contaminating proteins in toxoid preparations. Recent work has therefore concentrated on the development of procedures for the purification of toxins to near-homogeneity. The use of purified toxins in the production of vaccines, however, suffers from the drawbacks, first, of having to produce them under high containment and, secondly, of requiring the presence of low levels of formaldehyde to prevent possible reversion of the toxoid to the active state.

Production of subunit vaccines against other organisms and toxins has been investigated by a number of laboratories. This work has focused on the best known toxin subtypes, namely A and B, leading to new vaccines giving specific immunity against toxins of type A or B. Each new vaccine, however, may not give protection against other toxin subtypes.

Recombinant production of vaccine components has brought great advances in vaccine purity and volume of production. A. J. Makoff et al, in Bio/Technology, volume Oct. 7, 1989, pages 1043–1046, describe the expression of a tetanus toxin fragment in *E.coli*, and its purification and potential use as a vaccine. The technique described nevertheless requires a large number of steps to recover purified vaccine components from the host cells.

BRIEF SUMMARY OF THE INVENTION

It is an object of this invention to produce a vaccine against a type F *botulinum* toxin. It is another object to simplify vaccine manufacture. A further object is to improve production of *botulinum* toxin vaccines. A still further object of the invention is to overcome or at least mitigate problems and/or limitations in existing vaccines and methods of production.

DETAILED DESCRIPTION OF THE INVENTION

According to a first aspect of the invention there is provided a polypeptide free of *botulinum* toxin activity which induces protective immunity to a type F *botulinum* toxin. The polypeptide is useful in manufacture of a vaccine against type F toxin, and in contrast to prior art compositions such as polyvalent vaccines is not a toxoid and does not need pretreatment with formaldehyde. Also in contrast to prior art compositions the polypeptide is generally of smaller size than the toxin itself.

An embodiment of the first aspect of the invention provides a polypeptide characterized in that it:
  (a) is free of *botulinum* toxin activity, and
  (b) is capable of eliciting, in a mammal, an immunological response that is protective against type F *botulinum* toxin.

The term "protective" used in conjunction with "immunity" and "immunological response" is used to indicate an increased ability to survive challenge by active *botulinum* toxin F. This increase is typically mediated by an increased titre of antibodies to the toxin or an increased ability to produce antibodies to the toxin upon challenge with toxin. The term is not intended to indicate absolute protection against any amount of toxin.

The invention thus offers specific protection against a type F *botulinum* toxin, protection that has hitherto been unavailable.

In a particular embodiment the present invention provides a peptide or peptide conjugate comprising the amino acid sequence of the *C. botulinum* strain Langeland BoNT/F from amino acids 848 to 1278 (SEQ ID NO:1), but lacking the amino acid sequences of the L chain and $H_N$ epitopes necessary for metalloprotease activity and toxin internalisation (found between amino acids 1 to 439 and 440 to 847, respectively); the peptide is capable of inducing an immune response that is protective against BoNT/F when administered to humans or other animals.

In a more particular embodiment the peptides of the invention consist of substantially only the sequence of amino acids from 848 to 1278 (SEQ ID NO:1) of the amino acid sequence of BoNT/F of the *Clostridium botulinum* strain Langeland, or of that sequence in the form of a fusion peptide with another amino acid sequence not being amino acids 1 to 847 of BoNT/F. The term 'other amino acid sequence' will be understood by a person skilled in the art to include complete proteins as well as relatively short amino acid sequences as appropriate to the needs of the user. Optionally, the other amino acid sequence is a non-*C. botulinum*, antigenic protein which is included fused to the aforesaid sequence for the purpose of providing other immunity or labelling, or for modifying expression of the polypeptide in a host cell.

In another embodiment of the invention the polypeptide comprises a fragment or a derivative of a type F *botulinum* neurotoxin free of *botulinum* toxin activity and capable of inducing protective immunity against type F toxin. The fragment is free of toxoid and free of formaldehyde and has a length of less than 700 amino acids, preferably less than 500 amino acids.

In further specific embodiments of the invention the fragment is selected from:
 (a) amino acids 848–1278 of a type F *botulinum* toxin, (SEQ ID NO:1)
 (b) amino acids 848–991 of a type F *botulinum* toxin, (SEQ ID NO:2)
 (c) amino acids 992–1135 of a type F *botulinum* toxin, (SEQ ID NO:3) and
 (d) amino acids 1136–1278 of a type F *botulinum* toxin (SEQ ID NO:4).

The invention also relates to a toxin derivative, being a synthetic polypeptide comprising a plurality of fragments of a type F *botulinum* toxin linked together in repeated sections. The derivative can comprise a dimer of the fragments specified above.

The first aspect of the invention also provides polypeptide compositions, free of *botulinum* toxin activity and capable of inducing protective immunity against *botulinum* toxin, which compositions are adapted so as to facilitate their processing. This is of advantage in the manufacture of vaccines as polypeptide must be separated out from a mixture of any components that are undesirable in an eventual vaccine. Such an adapted composition comprises:
 (1) a polypeptide, free of *botulinum* toxin activity and capable of inducing protective immunity against a *botulinum* toxin; and
 (2) a polypeptide adapted for purification of the composition.

Component (2) is adapted, for example, to facilitate purification of the composition from aqueous solution and optionally comprises an antibody, a binding region of an antibody, a polypeptide adapted to bind to an ion exchange column, a polypeptide adapted to bind to an affinity chromatography column or a purification ligand.

The composition preferably comprises or consists of a single polypeptide including components (1) and (2), for example in the form of a fusion polypeptide.

In use of the compositions, extraction of the compositions from a mixture such as the supernatant from lysed cells expressing the composition is rendered a simple and fast process. It is particularly advantageous that in the composition, the vaccinating properties of component (1) are substantially retained, meaning that after purification of the composition it is used in a vaccine without the need for further modification, in particular without the need to remove component (2). As candidates for component (1) of the composition, all polypeptides previously described according to the first aspect of the invention are suitable. Further, fragments of tetanus toxin, free of toxin activity, are suitable.

A polypeptide according to a specific embodiment of the invention thus comprises a fusion protein of:
 (a) amino acids 848 to 1278 (SEQ ID NO:1) of a type F *botulinum* neurotoxin, with
 (b) a purification moiety.

It is preferred that the purification moiety is adapted to bind to an affinity chromatography column. A typical purification moiety comprises from 50 to 500 amino acids. In a specific embodiment the fusion protein comprises maltose-binding protein as the purification moiety. This fusion protein is particularly suitable for purification using an affinity chromatography column and has been found to have useful vaccinating properties, as described below.

According to a second aspect the invention provides a vaccine against a *botulinum* toxin, comprising a polypeptide of the first aspect of the invention and a pharmaceutically acceptable carrier.

Suitable carriers are known to a person of skill in the for preparation of the vaccine. In an embodiment hereinafter described the carrier includes Freund's adjuvant. Another suitable carrier component is precipitated alum salts.

In a third aspect of the present invention there is. provided a recombinant DNA encoding polypeptides of the invention. Such recombinant DNA is conveniently provided by PCR amplification of the DNA coding for the desired sequence, eg., $BoNT/F_{848-1278}$, using primers targeted at respective ends of the double stranded sequence. Optionally the template sequence used in PCR represents the natural clostridial gene. In a preferred embodiment of the invention, however, the sequence used is a synthetic sequence encoding the same amino acids as the natural clostridial protein but in which codon usage has been altered. It is preferred that the synthetic gene has a GC content of at least 40%, preferably at least 45% and most preferably at least 50%.

In the case of such a synthetic sequence, insertion into the chosen expression plasmid is achieved, in one embodiment of the invention, through the use of incorporated appropriate restriction endonuclease recognition sites positioned at the extremities of the DNA fragment during its construction.

By whatever means the recombinant DNA encoding the BoNT/F peptide is generated, it is ligated into a suitable expression vector at which stage genetic fusion to a desired fusion peptide encoding sequence occurs, if desired, and the resultant vector is introduced into a suitable cell line, eg., *E. coli* or a yeast such as *Pichia pastoris*. A cell line producing the desired product is selected through established procedures, eg., Western Blotting, or ELISA.

Fourth and fifth aspects of the invention provide respectively, a plasmid vector incorporating the DNA of the third aspect and a cell line comprising the plasmid and expressing the DNA.

The invention also provides a method for production of a toxin vaccine in which purification of active vaccinating agent is facilitated by its expression in combination with a polypeptide sequence adapted for purification. Accordingly, a sixth aspect of the invention provides a method for production of a toxin vaccine, said vaccine comprising a vaccinating polypeptide free of toxin activity and capable of inducing protective immunity against a toxin, wherein the method comprises expressing in a host cell a DNA sequence coding for a fusion protein, said fusion protein comprising said vaccinating polypeptide and a purification moiety, obtaining an extract from the host cell comprising the fusion protein, and purifying therefrom the fusion protein.

In preferred embodiment of the sixth aspect of the invention there is provided a method of producing a vaccine containing a polypeptide of the first aspect of the invention, comprising the steps of:

(a) expressing in a host cell a DNA encoding a fusion protein, said protein being a fusion of (i) a fragment of a *botulinum* toxin, said fragment being free of toxin activity and capable of inducing protective immunity against *botulinum* toxin, and (ii) a purification moiety adapted to bind to an affinity chromatography column, (b) obtaining from said host cell an extract comprising the fusion protein, and (c) purifying the fusion protein using an affinity chromatography column.

In use of an embodiment of the invention the fusion protein is removed from the column by elution with a substrate. The method optionally includes cleaving the fusion protein and retaining the toxin fragment. The method has been used specifically with type F toxin but applies also to all other *botulinum* toxins and to tetanus toxin.

By this method the invention enables a preparation of *botulinum* toxin type F fragment free of contamination by other clostridial proteins, these latter frequently contaminating prior art preparations derived from cultures of Clostridium bacteria.

The fusion protein or toxin fragment obtained is typically in a substantially pure form and suitable for incorporation into a vaccine or other pharmaceutical composition in a few simple steps.

It should be noted that the creation of certain fusion proteins comprising the BoNT/F-derived peptide is useful in the initial isolation BoNT/F, following which cleavage is optionally employed to purify the BoNT/F-related peptide. Where codons are added at the 5'-end of the BoNT/F-encoding DNA to aid in translation, these amino acids are optionally retained at the $NH_2$-terminal end of the final peptide, eg., those used to bring about secretion of the peptide or more simply the addition of an $NH_2$-terminal methionine to initiate translation.

A seventh aspect of the invention provides a method of making a pharmaceutical composition comprising:

(a) expressing in a host cell a DNA encoding a fusion protein, said protein being a fusion of (i) a *botulinum* toxin or a fragment thereof, free of toxin activity and capable of inducing protective immunity against *botulinum* toxin, and (ii) a purification moiety adapted to bind to an affinity chromatography column, (b) obtaining from said host cell an extract comprising the fusion protein, (c) purifying the fusion protein using an affinity chromatography column, (d) incorporating the purified fusion protein into a pharmaceutical composition.

The purification moiety typically comprises 50 to 500 amino acids, is water soluble and binds to an affinity chromatography column.

The inventors have found that a fusion protein retaining the purification moiety is of advantage in producing a vaccine against a type F *botulinum* toxin. Vaccinating activity is found in the fusion protein, so the purification protein does not need to be removed prior to vaccine manufacture, thus simplifying the manufacturing process. It is preferred that the purification protein is a globular, water soluble protein that binds to and can be purified using an affinity chromatography column. It is further preferred that the purification protein is highly immunogenic. Thus, a particularly preferred fusion protein comprises a fragment of a *botulinum* toxin free of toxin activity, an immunogenic region and a purification region adapted to bind to an affinity chromatography column.

The term immunogenic region is used above to describe a sequence of amino acids in a protein that is known to elicit stimulation of the immune system in humans or other animals. Examples of such an immunogenic region include keyhole limpet haemocyanin.

Further aspects of the invention provide a pharmaceutical containing the fusion protein, methods of vaccinating mammals using the vaccines and compositions of the invention and antisera raised against the polypeptides, vaccines and compositions of the invention.

BRIEF DESCRIPTION OF THE DRAWINGS

There now follows description of specific embodiments of the invention, illustrated by drawings in which.

SEQ ID NO:5 shows the nucleotide sequence of the region of the BoNT/F gene from *Clostridium botulinum* type F strain Langeland encoding the $H_C$-fragment;

SEQ ID NO:6 shows a synthetic DNA sequence encoding the BoNT/F $H_C$ fragment which uses codons which are used most frequently in highly expressed genes of *E. coli*. The codon corresponding to BoNT/F $Ser_{848}$ begins at nucleotide position 12. It is proceeded by a codon specifying a $NH_2$-terminal methionine codon and restriction sites for NdeI and BamHI. The codon for $Asn_{1278}$ begins at nucleotide position 1302, and is followed by a translational stop codon (nt 1305–1308) and a restriction site for XbaI;

EXAMPLES
Generation of a Synthetic DNA Fragment Encoding $H_C$ of BoNT/F Which Makes Use of Codons Utilised by Highly Expressed E. coli Genes A synthetic sequence encoding BoNT/$F_{848-1278}$ was designed by reverse translation of the BoNT/F amino acid sequence using the REVTRANS programme of DNASTAR Inc (Madison, USA). The codon code used was the "strongly expressed E. coli backtranslation code" (SECOLI.RTC). To facilitate the construction, a number of changes were then made to introduce restriction enzyme recognition sites at strategic points along the length of the fragment, including unique flanking proximal sites for BamHI and NdeI a distal flanking site for XbaI and internal sites for HpaI, MluI and SpII. The gene was then constructed from overlapping 100 mer oligonucleotides by a procedure essentially as described elsewhere [Sandhu et al (1992) Biotechniques 12:14–16].

Briefly, the gene was constructed as 4 individual blocks (A, B, C and D), each of approximately 350 bp in size. Each block was assembled from 4×100 mer alternating oligonucleotides which overlapped with each other by 20 nucleotides. These 4 oligonucleotides were used in a PCR to generate a composite c.350 bp double-stranded DNA fragment, which was subsequently amplified using 20 mer flanking primers. The amplified fragments of each block were then cloned directly into plasmid pCRII (invitrogen Corp). The flanking primers of all 4 blocks were designed to include restriction enzyme sites which would allow their subsequent assembly into B by HpaI (5') and MluI (3'), block C by MluI (5') and SpII (3'), and block D by SpII (5') and XbaI (3'). Each block was, therefore, released from their respective pCRII-derived recombinant plasmid by cleavage with the appropriate enzyme and the isolated fragments ligated to pMTL23 [Chambers et al (1988). Gene 68:139–149] plasmid DNA which had been cleaved with BamHI and XbaI. A clone was then selected in which all 4 blocks had been inserted in the expected order. This was confirmed by nucleotide sequencing using routine methods [Maniatis et al. (1989). Molecular Cloning a Laboratory Manual. Cold Spring Harbor Laboratory Press], and the plasmid obtained designed pFHC23.

Generation of a $H_C$ Peptide (848 to 1278) of BoNT/F of C. botulinum Strain Langeland A candidate vaccine against the BoNT/F of C. botulinum was produced by expressing the fragment of the synthetic gene encoding the $H_C$ fragment, amino acids 848 to 1278. This DNA fragment was isolated from plasmid pFHC23 as an approximately 1.3 kb BamHI-XhoI restriction fragment and inserted between the unique BamHI and SalI sites of pUC9 [Vieira and Messing (1982). Gene 19: 259–268], generating the plasmid pFHC29. The insert was then reisolated from pFHC29 as an EcoRI-XbaI fragment and inserted between the equivalent sites of the commercially available expression vector pMaI-c2 (New England Biolabs), to yield the final plasmid pFHC206. The resultant plasmid expressed BoNT/$F_{848-1278}$ as a fusion protein with the vector encoded malaise binding protein (MBP).

Fusion protein product (MBP-BoNT/$F_{848-1278}$) was prepared from the cell line containing pFHC206 in the following manner. E. coli containing pFHC206 was cultivated in 1 liter of media (M9, supplemented with 0.8M sorbitol, 0.5% casamino acids, 50 µg/ml ampicillin), shaking (200 rpm) at 37° C. until an $OD_{600}$ of 1.0 was achieved. At this point IPTG was added at a final concentration of 1 mM and shaking continued at 27° C. for a further 4 hour. Cells were harvested by centrifugation (5000×g) and resuspended in 20 ml of lysis buffer (Protein Fusion and Purification System, New England Biolabs) and cells disrupted by sonication. Lysate was applied to a GPC column containing 180 ml of Sephacel S100, and the protein in the void fraction collected. MBP-BoNT/F $H_{848-1278}$ fusion protein in this fraction was then allowed to adsorb at room temperature to a 4–6 ml volume of Amylose resin (New England Laboratories) over a 3 hour period with gentle shaking (10 rpm). Recombinant fusion protein was then eluted in buffer (0.01 M Tris HCl, pH 7.0) containing 5 mM malaise. Eluted protein was concentrated using an Amicon PM30 membrane filter.

Toxicity of Candidate Vaccine

The toxicity of the candidate vaccine fusion peptide was determined by intraperitoneal inoculation of 25 µg amounts of the total recombinant MBP-BoNT/$F_{848-1278}$ protein into groups of 4 mice. The candidate vaccine was well tolerated and mice showed no signs of acute or chronic toxicity up to 2 weeks post inoculation.

Antibody Responses to Candidate Vaccines

Figure 1:
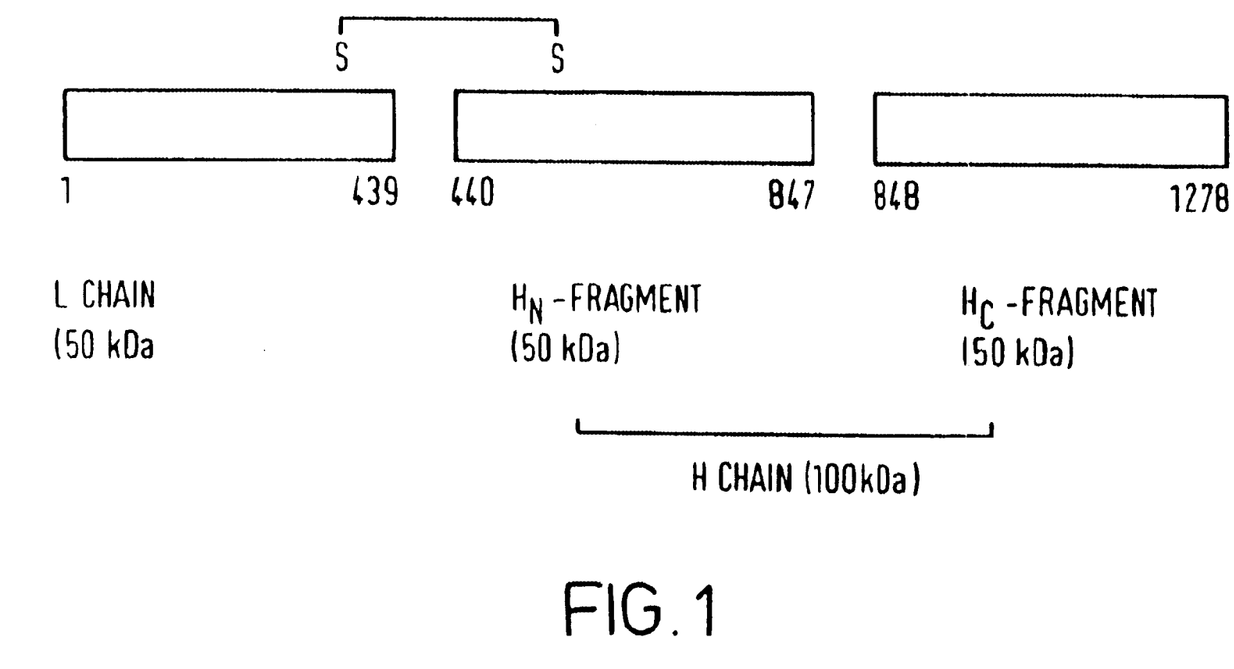
FIG. 1: shows the three major domains of a BoNT toxin. The numbers refer to the positions of the amino acids flanking these three domains in BoNT/F of *C. botulinum* strain Langeland.
Figure 2:
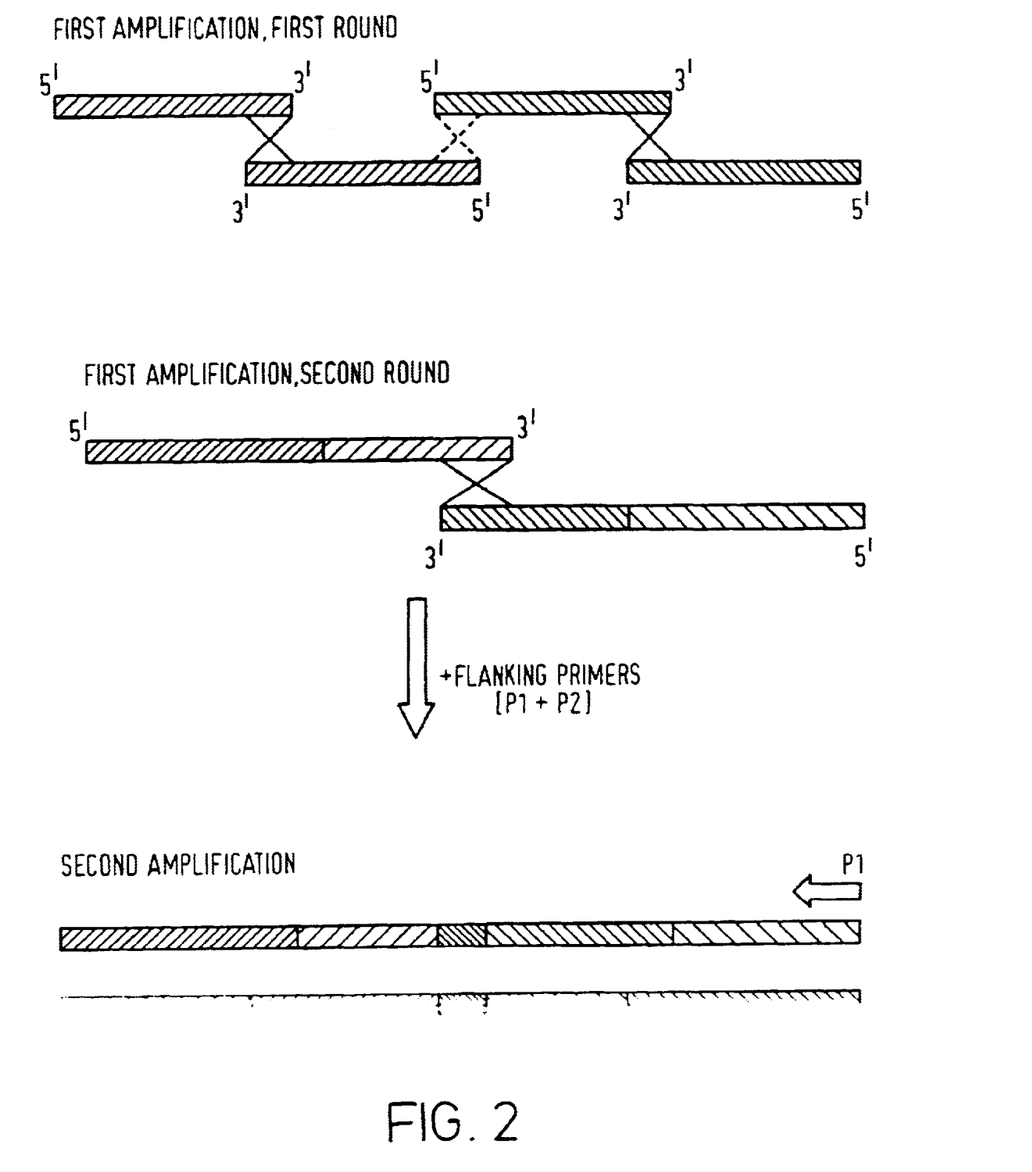
FIG. 2: shows a schematic representation of how synthetic gene blocks were assembled by PCR.
Figure 3:
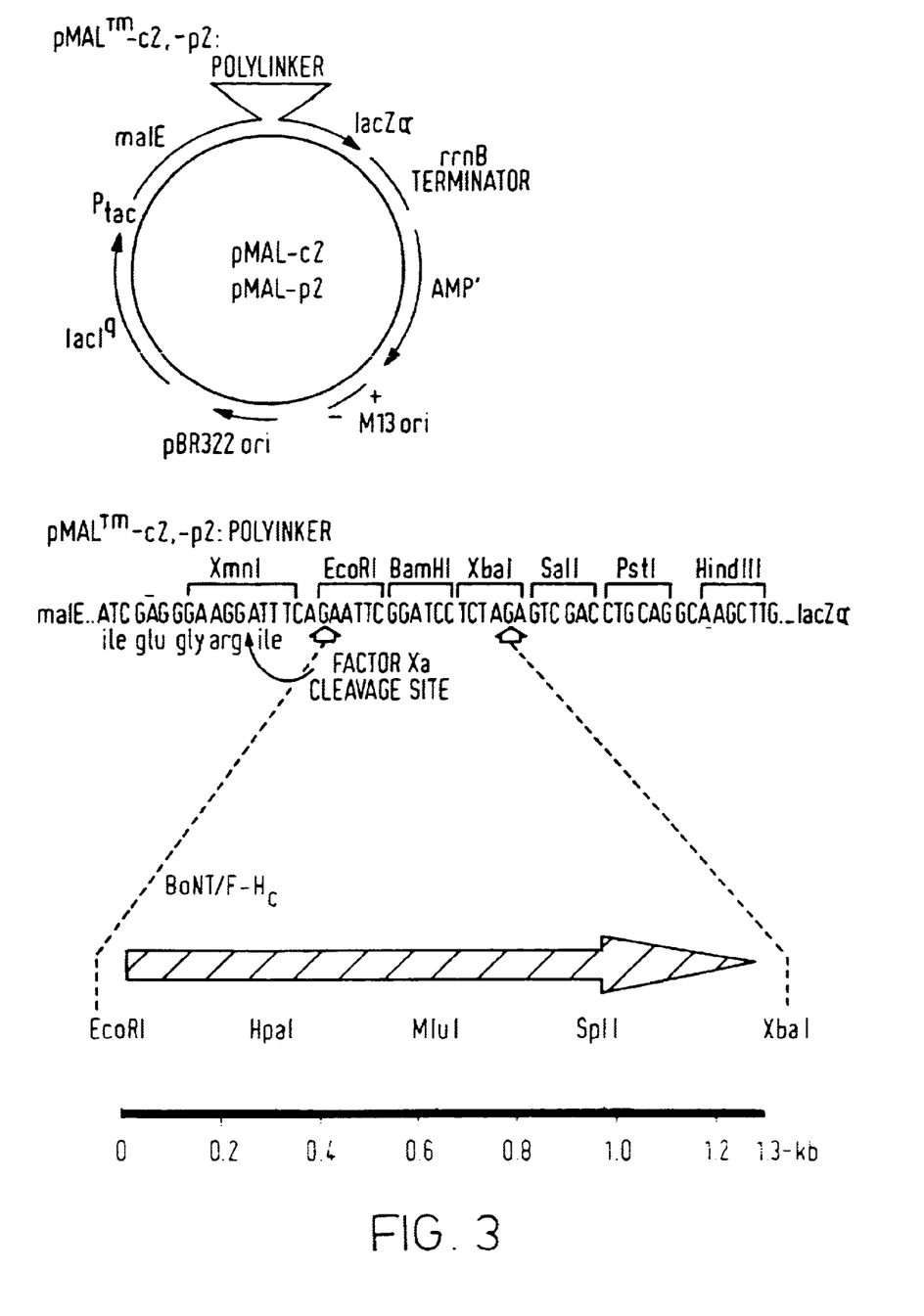
FIG. 3: shows an example of a recombinant plasmid (pFHC206) made in which the synthetic DNA fragment of FIG. 5 is inserted into the expression plasmid pMaI-C2; (SEQ ID NOs:7 (DNA) and 8 (amino acid) and FIG. 4: shows antibody titres against BoNT/F obtained in mice immunised with MBP-BoNT/$F_{848-1278}$ recombinant protein.
Figure 4:
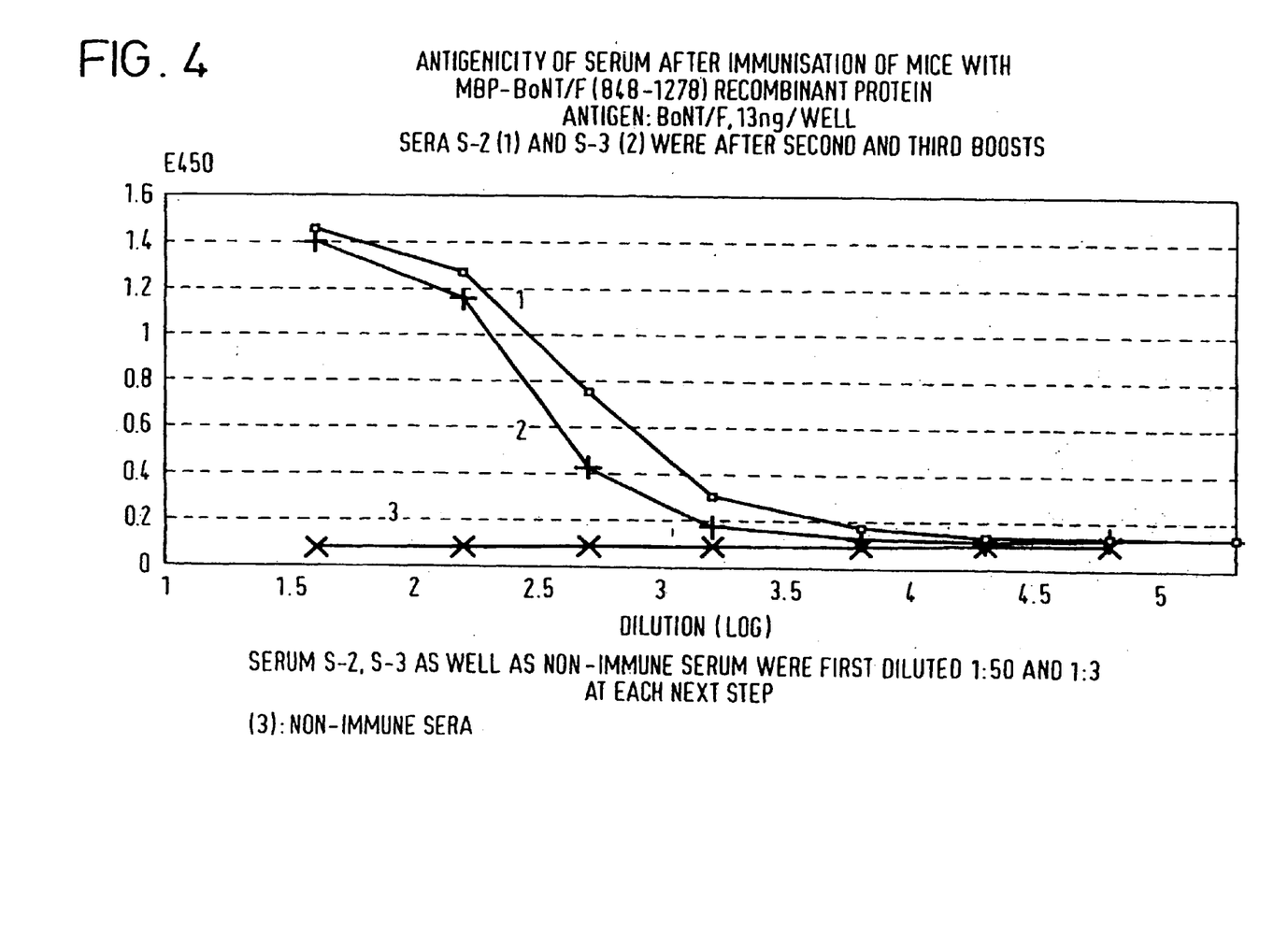

The candidate vaccine was administered to groups of 4 mice by intraperitoneal inoculation in complete Freund's adjuvant, and a booster inoculation given on 3 further occasions at two week intervals. Antibody response against purified C. botulinum strain Langeland BoNT/F was monitored by ELISA (FIG. 4).

Protection Against Toxin Challenge

Animals which were immunised with MBP-BoNT/$F_{848-1278}$ fusion protein were subjected to an intraperitoneal challenge with various doses of purified C. botulinum strain Langeland BoNT/F. At doses of 12 $LD_{50}$ and above, all the control, unimmunised mice succumbed within 24 hour. All immunised groups of mice survived challenges of up to $2.4×10^4$ $LD_{50}$. One of the immunised mice which had survived an initial challenge of 1.8, $LD_{50}$ was subsequently shown to be immune to a further challenge of $10^6$ $LD_{50}$.

TABLE 1

Protection against challenge with C. botulinum strain Langeland BoNT/F afforded by the MBP-BoNT/$F_{848-1278}$ fusion protein vaccine. A total of 4 × 25 µg intraperitoneal doses of antigen mixed with adjuvant were given to groups of 4 mice at 14 day intervals. After 50 days mice were subjected to intraperitoneal challenges of varying levels of purified BoNT/F, (isolated from C. botulinum strain Langeland), and deaths recorded up to 4 days.

| | Mortality/Total Animals | |
| --- | --- | --- |
| Challenge Dose ($LD_{50}$) | Control Animals | Immunised Animals |
| 2.4 × 10⁴ | 4/4 | 0/4 |
| 3.6 × 10³ | 4/4 | 0/4 |
| 5.4 × 10² | 4/4 | 0/4 |
| 81 | 4/4 | 0/4 |
| 12 | 4/4 | 0/4 |
| 1.8 | 2/4 | 0/4[a] |

[a] = one of the surviving individuals from this group was subsequently shown to be protected against a BoNT/F challenge equivalent to $10^6$ $LD_{50}$.

This invention provides a fragment (such as amino acids 848–1278) of BoNT/F isolated from C. botulinum strain Langeland for use as a vaccine. The fragment retains its immunogenic properties while still fused with MBP, dispensing with the need for an additional purification step. The recombinant fusion protein appears to be non-toxic in mice at doses up to 25 µg. Repeated doses produced a significant antibody response which protects animals against BoNT/F challenge. As a vaccine it offers several advantages over neurotoxin toxoided by formaldehyde treatment. Most notably, it may be prepared more easily and, due to the absence of active toxin, at a lower level of containment. The absence of other contaminating C. botulinum proteins and partially toxoided materials also make it inherently safer for vaccine application and less reactogenic.

What is claimed is:

1. An isolated polypeptide comprising a sequence of no more than 700 consecutive amino acids of a type F *botulinum* toxin sequence, which comprises a sequence of amino acids selected from the group consisting of:
   (a) amino acids 848–1278 of a type F *botulinum* toxin (SEQ ID NO: 1)
   (b) amino acids 992–1135 of a type F *botulinum* toxin (SEQ ID NO: 3), and;
   (c) amino acids 1136–1278 of a type F *botulinum* toxin (SEQ ID NO: 4).

2. An isolated polypeptide comprising a dimer of a polypeptide comprising no more than 700 consecutive amino acids of a type F *botulinum* toxin sequence, which comprises a sequence selected from the group consisting of:
   (a) amino acids 848–1278 of a type F *botulinum* toxin (SEQ ID NO: 1)
   (b) amino acids 848–991 of a type F *botulinum* toxin (SEQ ID NO: 2)
   (c) amino acids 992–1135 of a type F *botulinum* toxin (SEQ ID NO: 3), and
   (d) amino acids 1136–1278 of a type F *botulinum* toxin (SEQ ID NO: 4).

3. A polypepticle composition comprising:
   (1) an isolated polypeptide according to claim 1, and
   (2) an isolated polypeptide that facilitates or enhances purification of the polypeptide of (1).

4. An isolated fusion protein comprising a sequence of amino acids selected from the group consisting of SEQ ID NO:1, SEQ ID NO:2, SEQ ID NO:3, and SEQ ID NO:4, fused to a polypeptide that facilitates or enhances purification.

5. A fusion protein according to claim 4 wherem said polypeptide that facilitates or enhances purification is a polypeptide that binds a chromatography column.

6. A fusion protein according to claim 5 wherein said chromatography column is an affinity chromatography column.

7. A fusion protein according to claim 4 which comprises SEQ ID NO:1 fused to a purification moiety.

8. A vaccine comprising a pharmaceutically acceptable carrier and a polypeptide comprising no more than 700 consecutive amino acids of a type F *botulinum* toxin sequence, which comprises a sequence selected from the group consisting of:
   (a) amino acids 848–1278 of a type F *botulinum* toxin (SEQ ID NO:1),
   (b) amino acids 848–991 of a type F *botulinum* toxin (SEQ ID NO:2),
   (c) amino acids 992–1135 of a type F *botulinum* toxin (SEQ ID NO:3), and
   (d) amino acids 1136–1278 of a type F *botulinum* toxin (SEQ ID NO:4).

9. A recombinant DNA encoding a polypeptide according to claim 1.

10. A method of producing a polypeptide according to claim 4 comprising the steps of:
    (a) expressing in a host cell a DNA encoding a fusion protein according to claim 4,
    (b) obtaining from said host cell an extract comprising the fusion protein, and
    (c) purifying the fusion protein using a chromatography column.

11. A method according to claim 10 wherein the fusion protein is removed from the column by elution with a substrate.

12. A method according to claim 10 further comprising cleaving the fusion protein and retaining the toxin fragment.

13. A method of making a pharmaceutical composition comprising:
    (a) expressing in a host cell a DNA fragment encoding a fusion protein according to clalm 4,
    (b) obtaining from said host cell an extract comprising the fusion protein,
    (c) purifying the fusion protein using a chromatography column, and
    (d) incorporating the purified fusion protein into a pharmaceutical composition.

14. A method according to claim 13 wherein the fusion protein comprises a purification moiety that bind to an affinity chromatography column.

15. A pharmaceutical composition comprising a fusion protein according to claim 4, and
    a pharmaceutically acceptable carrier.

16. A pharmaceutical composition according to claim 15 wherein the fusion protein comprises a polypeptide that binds to an affinity chromatography column.

17. A recombinant DNA encoding a fusion protein according to claim 4.

18. The fusion protein of claim 4 wherein the sequence of amino acids is selected from the group consisting of SEQ ID NO: 2, SEQ ID NO: 3, and SEQ ID NO: 4.

19. A method of producing antibodies in a mammal against *botulinum* toxin, comprising administering to said mammal a vaccine according to claim 8.

20. A method of producing antibodies in a mammal against *botulinum* toxin, comprising administering to said mammal a composition of claim 15.

21. A method of vaccinating a mammal against a *botulinum* toxin, said method comprising administering to said mammal a polypeptide comprising no more than 700 consecutive amino acids of a type F *botulinum* toxin sequence, which includes a sequence selected from the group consisting of:
(a) amino acids 848–1278 of a type F *botulinum* toxin (SEQ ID NO:1)
(b) amino acids 848–991 of a type F *botulinum* toxin (SEQ ID NO:2)
(c) amino acids 992–1135 of a type F *botulinum* toxin (SEQ ID NO:3), and;
(d) amino acids 1136–1278 of a type F *botulinum* toxin (SEQ ID NO:4).

22. A method according to claim 21 wherein the said sequence is fused to a polypeptide that facilitates or enhances purification.

23. A method according to claim 21 wherein said polypeptide comprises no more than 500 consecutive amino acids of a type F *botulinum* toxin sequence.

24. A method according to claim 21 wherein said polypeptide consists of a sequence of amino acids selected from the group consisting of:
(a) amino acids 848–1278 of a type F *botulinum* toxin (SEQ ID NO:1)
(b) amino acids 848–991 of a type F *botulinum* toxin (SEQ ID NO:2)
(c) amino acids 992–1135 of a type F *botulinum* toxin (SEQ ID NO:3), and;
(d) amino acids 1138–1278 of a type F *botulinum* toxin (SEQ ID NO:4), which sequence is optionally fused to a polypeptide that facilitates or enhances purification.

25. A method according to claim 24 wherein the polypeptide consists of SEQ ID NO:1.

26. A method according to claim 21 wherein the polypeptide is in the form of a dimer.

27. An isolated polypeptide consisting of amino acids 848–991 of a type F *botulinum* toxin (SEQ ID NO:2) optionally fused to a polypeptide that facilitates or enhances purification.

28. A recombinant DNA encoding a polypeptide according to claim 27.

* * * * *